United States Patent
Dake et al.

(10) Patent No.: US 10,566,083 B2
(45) Date of Patent: Feb. 18, 2020

(54) USED NARCOTIC OR CONTROLLED SUBSTANCE CONTAINER RETURN AND TRACKING FOR AUTOMATED MEDICATED DISPENSING MACHINES

(71) Applicant: TOUCHPOINT MEDICAL, INC., Concordville, PA (US)

(72) Inventors: Martin William Dake, Oldsmar, FL (US); Jun Yue, Shaanxi (CN); Dan Zhao, Shaanxi (CN); Tiansun Wu, Shanghai (CN)

(73) Assignee: TOUCHPOINT MEDICAL, INC., Concordville, PA (US)

(*) Notice: Subject to any disclaimer, the term of this patent is extended or adjusted under 35 U.S.C. 154(b) by 0 days.

(21) Appl. No.: 15/761,173

(22) PCT Filed: Sep. 21, 2015

(86) PCT No.: PCT/CN2015/090155
§ 371 (c)(1),
(2) Date: Mar. 19, 2018

(87) PCT Pub. No.: WO2017/049435
PCT Pub. Date: Mar. 30, 2017

(65) Prior Publication Data
US 2018/0261312 A1    Sep. 13, 2018

(51) Int. Cl.
*G16H 20/13*    (2018.01)
*G05B 15/02*    (2006.01)
(Continued)

(52) U.S. Cl.
CPC ............. *G16H 20/13* (2018.01); *G05B 15/02* (2013.01); *G06Q 10/083* (2013.01); *G06Q 50/22* (2013.01)

(58) Field of Classification Search
CPC ...... G16H 20/13; G06Q 50/22; G06Q 10/083; G05B 15/02
(Continued)

(56) References Cited

U.S. PATENT DOCUMENTS 5,961,036 A    10/1999    Michael et al.
8,027,749 B2 *  9/2011    Vahlberg ............... G06Q 10/087
                                                    700/244
(Continued)

FOREIGN PATENT DOCUMENTS

CN    104334052 A    2/2015

OTHER PUBLICATIONS

International Search Report issued in PCT/CN2015/090155 dated Jun. 15, 2016, 3 pages.
(Continued)

*Primary Examiner* — Michael Collins
(74) *Attorney, Agent, or Firm* — RatnerPrestia

(57) ABSTRACT

A system includes a database that stores information associated with a medication located in a base station. The information includes an indication of whether a container of the medication was returned to the base station subsequent to the medication being administered. A control module communicates with the base station, determines when the medication is retrieved from the base station, determines whether the container of the medication is returned to the base station, and updates the information stored in the database when the container of the medication is returned to the base station.

18 Claims, 3 Drawing Sheets

(51) Int. Cl.
*G06Q 50/22* (2018.01)
*G06Q 10/08* (2012.01)

(58) Field of Classification Search
USPC .................................................. 700/231–244
See application file for complete search history.

(56) References Cited

U.S. PATENT DOCUMENTS

| | | | | |
|---|---|---|---|---|
| 8,073,563 B2* | 12/2011 | Vahlberg | ............... | G06Q 10/087 700/244 |
| 8,126,590 B2* | 2/2012 | Vahlberg | ............... | G06Q 10/087 700/241 |
| 8,131,397 B2* | 3/2012 | Vahlberg | ............... | G06Q 10/087 700/236 |
| 8,140,186 B2* | 3/2012 | Vahlberg | ............... | G06Q 10/087 700/242 |
| 8,155,786 B2* | 4/2012 | Vahlberg | ............... | G06Q 10/087 700/244 |
| 8,239,062 B2* | 8/2012 | Vahlberg | ............... | G06Q 10/087 700/236 |
| 8,342,400 B1* | 1/2013 | Reese | ................. | G06F 19/3462 235/385 |
| 2006/0089858 A1 | 4/2006 | Ling | | |
| 2008/0319581 A1* | 12/2008 | Vahlberg | ............... | G06Q 10/087 700/242 |
| 2009/0187274 A1* | 7/2009 | Higham | ............ | G07C 9/00912 700/237 |
| 2013/0085766 A1 | 4/2013 | Bojarski et al. | | |
| 2013/0282401 A1* | 10/2013 | Summers | ............ | G06F 19/3456 705/3 |
| 2014/0278508 A1* | 9/2014 | Akdogan | ............... | A61J 7/0076 705/2 |
| 2015/0227127 A1* | 8/2015 | Miller | ................. | G05B 19/042 700/244 |

OTHER PUBLICATIONS

International Written Opinion issued in PCT/CN2015/090155 dated Jun. 15, 2016, 4 pages.
Notification of Reexamination of Chinese Application No. 201520834796.0, dated Mar. 22, 2018 with translation, 9 pages.
Chinese Office Action issued in Chinese Patent Application No. 201821932283.3 dated Nov. 27, 2019 with translation, 6 pages.

* cited by examiner

USED NARCOTIC OR CONTROLLED SUBSTANCE CONTAINER RETURN AND TRACKING FOR AUTOMATED MEDICATED DISPENSING MACHINES

CROSS REFERENCE TO RELATED APPLICATIONS

This application is the U.S. National Phase Application of PCT/CN2015/090155, filed Sep. 21, 2015, the contents of such application being incorporated by reference herein.

FIELD

The present disclosure relates to systems and methods for managing and tracking the return of containers for controlled pharmaceuticals and medical supplies.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Pharmaceuticals and medical supplies may be provided within a healthcare facility. For example, in a healthcare facility, pharmaceuticals (e.g., medications) and other medical supplies are distributed from a central distribution location (e.g., a central pharmacy) using a medication management system. Medication management systems may be classified as centralized medication management systems or decentralized medication management systems. For example, in a centralized medication management system, medications may be provided from the central pharmacy directly to a healthcare professional (e.g., a nurse) that will be administering the medications to respective patients.

Conversely, in a decentralized medication management system, multiple medication dispensing sites are located remotely from a centralized distribution location, such as a facility's pharmacy. The remote dispensing sites, such as a nurses' station in a hospital ward, serve as base stations from which healthcare professionals can readily access medications or other medical supplies to be administered to the patients under their care. A decentralized medication management system may implement a decentralized medication dispensing system (MDS). In some implementations, the MDS may correspond to an automated dispensing machine (ADM) that stores medications in secure transportable compartments.

Information associated with the pharmaceuticals and medical supplies may be managed and/or tracked. Example information tracked for pharmaceuticals and medical supplies include, but is not limited to, inventory, location, patient prescription information, associated healthcare professional, etc.

SUMMARY

A system includes a database that stores information associated with a medication located in a base station. The information includes an indication of whether a container of the medication was returned to the base station subsequent to the medication being administered. A control module communicates with the base station, determines when the medication is retrieved from the base station, determines whether the container of the medication is returned to the base station, and updates the information stored in the database when the container of the medication is returned to the base station.

In other features, the information further includes at least one of a time that the medication was retrieved from the base station, a time that the medication was administered to a patient, and a time that the container of the medication was returned to the base station. The information further includes an identifier associated with the container of the medication. The information further includes an identifier of a drawer in the base station.

In other features, the drawer is assigned to be used for storing the container of the medication. The control module assigns the drawer to be used for storing the container of the medication in response to an indication that the container of the medication is being returned to the base station. The information includes a total number of containers stored within the drawer. The control module provides a command to open the drawer in response to an indication that the container of the medication is being returned to the base station. The information includes respective indications from a healthcare professional and a witness that the container of the medication was returned to the base station.

A method includes storing, in a database, information associated with a medication located in a base station. The information includes an indication of whether a container of the medication was returned to the base station subsequent to the medication being administered. The method further includes determining when the medication is retrieved from the base station, determining whether the container of the medication is returned to the base station, and updating the information stored in the database when the container of the medication is returned to the base station.

In other features, the information further includes at least one of a time that the medication was retrieved from the base station, a time that the medication was administered to a patient, and a time that the container of the medication was returned to the base station. The information further includes an identifier associated with the container of the medication. The information further includes an identifier of a drawer in the base station.

In other features, the method further includes assigning the drawer to be used for storing the container of the medication. The method further includes assigning the drawer to be used for storing the container of the medication in response to an indication that the container of the medication is being returned to the base station. The information includes a total number of containers stored within the drawer. The method further includes providing a command to open the drawer in response to an indication that the container of the medication is being returned to the base station. The information includes respective indications from a healthcare professional and a witness that the container of the medication was returned to the base station.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Medications (and/or other medical supplies) may be transported within a facility using a mobile workstation (e.g., a point of care, or POC, workstation, medication cassettes, etc.) or other transport device, or may be carried by a healthcare professional. In example systems, the medications are transferred from a central pharmacy to a healthcare professional and transported by the healthcare professional to a base station (e.g., an automated dispensing machine, or ADM) and then from the base station to patients, and/or directly from the pharmacy to the patients, using the workstation, cassettes, etc.

Information associated with the medications may be tracked and stored during the transportation and administering of the items within the healthcare facility. For example, the information may be tracked using wireless communication connectivity (e.g., Wi-Fi, Bluetooth, RFID, or other wireless connectivity protocols) between the transport device and/or specific items and one or more databases that store the information. The information may be managed (e.g., monitored, updated, tracked, accessed, etc.) using mobile devices including, but not limited to, smartphones, tablet computers, laptop computers, other portable electronic devices, mobile workstations, etc.

Systems and methods according to the principles of the present disclosure track and store information associated with certain predetermined types of medications. For example, the predetermined types of medications may correspond to medications including narcotics or other controlled substances, and/or merely types of medications identified as items of interest within a particular healthcare facility. For example, some healthcare facilities may require that empty or opened containers/packaging for certain medications are returned to the central pharmacy or the base station after the medication has been administered to a patient or otherwise disposed of.

Accordingly, the systems and methods described herein provide a secure location for the return of used containers (e.g., packaging, vials, ampoules, syringes, etc.) after the medications have been administered, as well as associated tracking and storing of information related thereto. The information may include, but is not limited to, quantities of a medication retrieved, quantities of containers of that medication returned to the secure location, and/or information about transactions (i.e., returns of containers, such as quantities, times the containers were returned, locations, healthcare professionals that returned the containers, patients the containers were associated with, etc.). The secure location may be, for example only, a predetermined (i.e., dedicated) drawer in a base station and/or a drawer that is assigned when a healthcare professional attempts to return a container.

Figure 2:
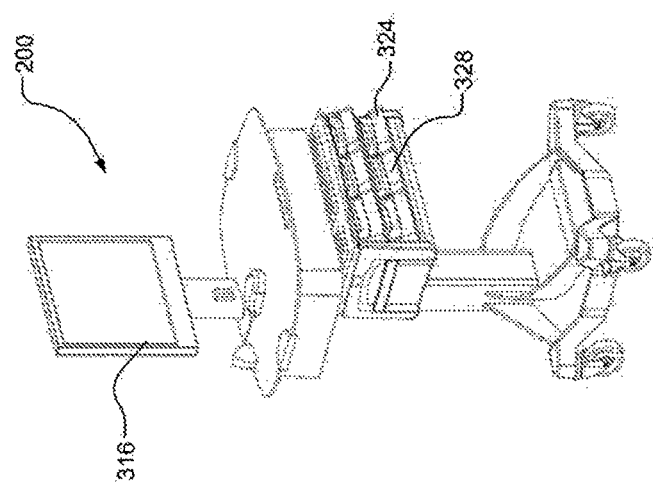
FIG. 2 is an example mobile POC workstation.
Figure 1:
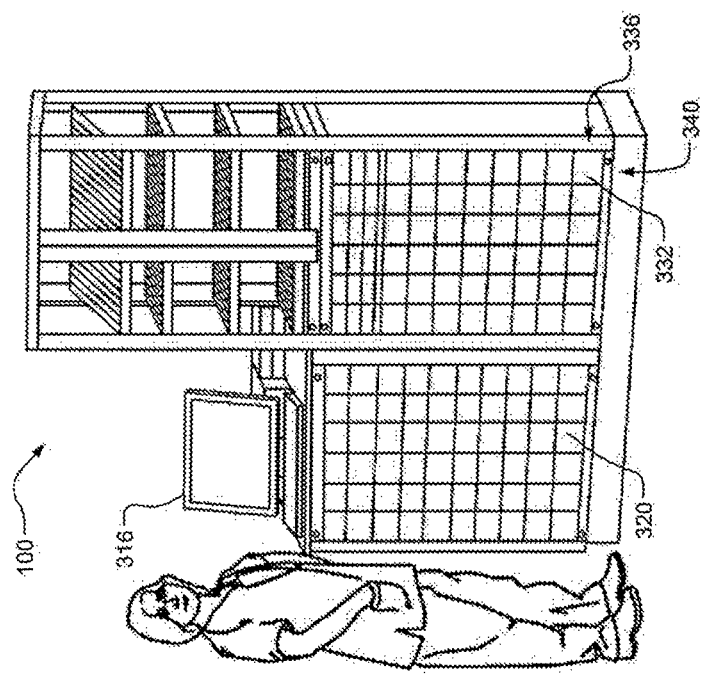
FIG. 1 is an example ADM.
Figure 3:
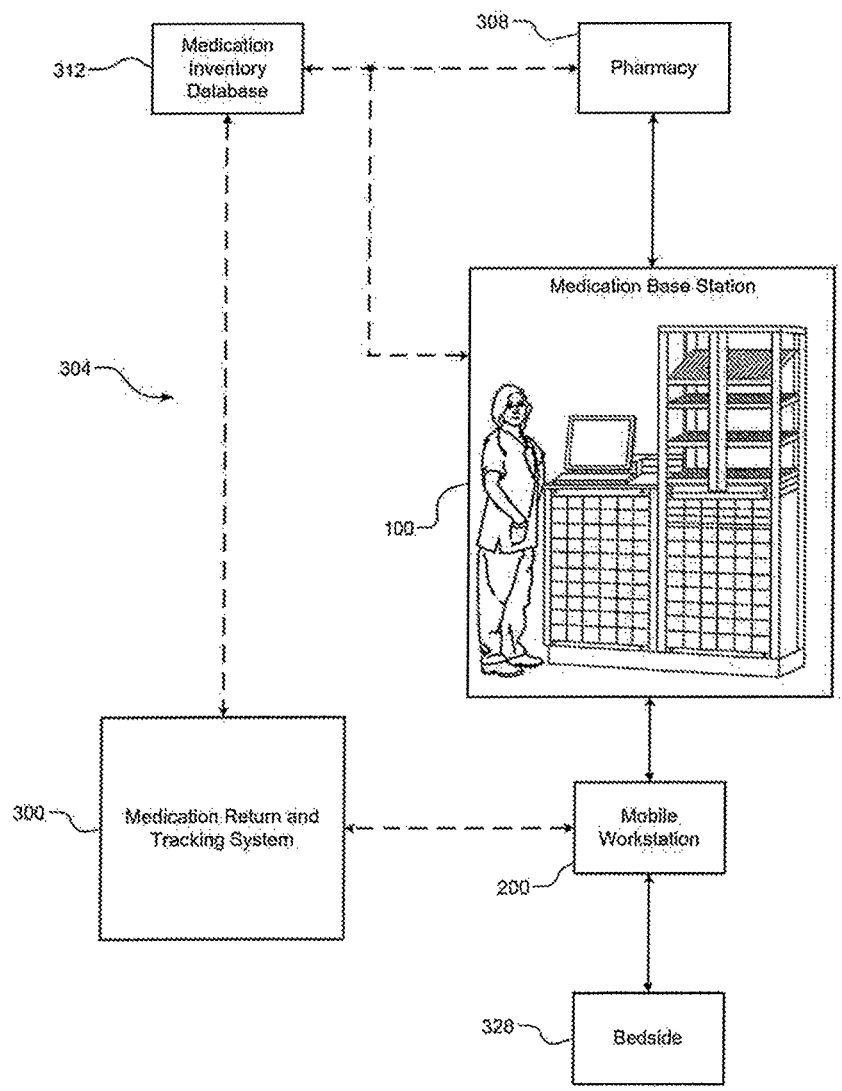
FIG. 3 is an example medication management system according to the principles of the present disclosure.

Referring now to FIGS. 1-3, FIGS. 1 and 2 show an example medication base station 100 and mobile POC workstation 200, respectively. FIG. 3 shows an example return and tracking system 300 according to the principles of the present disclosure operating within a medication management system 304. While the medication management system 304 is described as a decentralized medication management system, the return and tracking system 300 may also be implemented in a centralized medication management system or hybrid medication management system. Accordingly, as described, the example medication management system 304 includes the medication base station 100 and the mobile workstation 200.

In an example implementation, medications are provided from a central pharmacy 308 to one or more medication base stations 100. A central inventory database 312 stores inventory data about the medications, such as stock quantities of each medication available in the healthcare facility, locations of the medications (e.g., stock quantities of each medication in the central pharmacy 308 and/or in respective medication base stations 100, etc.). At the medication base station 100, the healthcare professional accesses either the mobile workstation 200 or the medication base station 100 according to facility protocols (e.g., by utilizing a user access control module 316 on one of the workstation 200 or base station 100). The healthcare professional then obtains information related to one or more medications prescribed for a particular patient. The information about patient specific medication is placed in a queue that can be accessed by the control module 316, as appropriate.

In one example implementation, as the healthcare professional approaches the base station 100 with the mobile workstation 200, the base station 100 and the workstation 200 may negotiate a communication link. After the communication link is secured, the base station 100 receives or reads the information in the queue containing the information about patient-specific medication and prescription information for a given patient. The base station 100 then enables access by the healthcare professional to respective storage locations (e.g., drawers 320) containing the particular medications for that patient. At the same time the mobile workstation 200 enables access by the healthcare professional to the patient specific drawer 324 for that patient on the mobile workstation 200.

The healthcare professional then retrieves the medications from the drawers 320 of the base station 100 and may record the retrieval activity according to facility protocols. The healthcare professional then places those medications in the patient-specific drawer 324 on the mobile workstation 200 and may record that activity according to facility protocols. These steps are repeated for each of the medications for the patient that are retrieved from the base station 100 and placed in the patient specific drawer 324 on the mobile workstation 200. Then the steps may also be repeated for any number of patients under the care of the healthcare professional.

The healthcare professional can thereafter administer the medications to the patient at the patient's bedside 328. For example, the healthcare professional transports the mobile workstation 200 to the patient. At that time, the healthcare professional can access the mobile workstation 200 according to facility protocols utilizing the control module 316 on the workstation 200. The healthcare professional then selects the patient for administration of medications. The control module 316 then enables access by the healthcare professional to the patient-specific drawer 324 containing the medications for that patient. The healthcare professional then removes the medications from the patient-specific drawer 324 and administers the medications to the patient according to facility protocols (e.g., according to the well-known "five rights" protocol). This may include using the control module 316 to record that the medications have been administered. Once the medications are administered to the first patient, the healthcare professional can then proceed to successive patients whose medications are contained in the mobile workstation 200, if any.

Either or both of the medication base station 100 and the mobile workstation 200 may be configured to communicate with peripheral devices, such as bar code readers, PDAs, biometric security devices (e.g., a fingerprint scanner), scanners, card readers, keyboards, RFID systems, and the like. The medication base station 100 and/or the mobile workstation 200 (e.g., via respective control modules 316) may implement the operating protocols of the healthcare facility for managing the distribution of medications from a pharmacy to a patient.

The return and tracking system 300 monitors, tracks, generates and/or stores data about medication containers subsequent to the corresponding medications being administered to respective patients or otherwise disposed (i.e., "wasted"). For example, upon administering the medication or indicating that the medication is to be wasted, the healthcare professional may be prompted (e.g., using a respective display of the workstation, a handheld device, etc.) to return the container to a dedicated drawer 332 (or, one of a dedicated row of drawers 336, one of a dedicated column of drawers 340, etc.) in the base station 100. The drawer 332 may be pre-assigned to be used for returned containers, or any one of the drawers 320 may be assigned to be used for returns at any time. For example, the drawer 332 may be assigned to be used for returned containers in response to a healthcare professional indicating that a medication has been administered, when a healthcare professional accesses the base station 100 to return a container, when a previously assigned drawer is full, etc. When the drawer 332 is emptied (e.g., by pharmacy staff or another healthcare professional), the drawer 332 may continue to be assigned to returned medication containers or may be reassigned to general use.

The return and tracking system 300 is configured to implement various functions corresponding to the medication containers. For example, the return and tracking system 300 may store data indicating a quantity of returned medication containers in the drawer 332. The quantity may be based on user input (e.g., an indication, received from a healthcare professional and/or the base station 100, that a medication container was placed in the drawer) and/or sensors or other devices (e.g., cameras) configured to count a number of medication containers within the drawer 332. For example, the sensors or other devices may verify that a weight of contents of the drawer 332 increased in response to a healthcare professional indicating that a medication container was returned. The weight may be compared to a calculated weight corresponding to known weights of all items purportedly contained within the drawer 332. The return and tracking system 300 may verify the quantity of the items within the drawer 332 each time the drawer 332 is opened, each time a medical container is returned to the drawer 332, each time an item is removed from the drawer and/or the drawer 332 is emptied, etc.

In some implementations, the healthcare professional may be prompted to count the number of medication containers within the drawer 332 each time the drawer 332 is opened. For example, when returning a medication container to the drawer, the healthcare professional may be required to count the total number of medication containers including the newly returned medication container, and to provide information indicating the totally quantity of medical containers in the drawer 332.

The healthcare professional may be prompted to input the number of medication containers being returned to the drawer 332. For example, the healthcare professional may return one or more of a total number of medication containers retrieved from the base station 100 at an earlier time. If the number of medication containers being returned is not the same as the total number of medication containers retrieved, then the system 300 may prompt the healthcare professional to provide a reason for the discrepancy. For example, the healthcare professional may manually enter a reason and/or select from a list of predetermined reasons using the control module 316.

The system 300 may store information associating each medication container with a unique medication and/or a specific healthcare professional, patient, etc. For example, each medication container may have an associated identifier. Accordingly, each medication container may only be returned a single time. For example, the system 300 may store information indicating that the medication has been retrieved by a healthcare professional and has not yet been administered. The system 300 may update this information when the medication has been administered to indicate that the medication has been administered but not yet returned. The system 300 again updates this information when the corresponding medication container has been returned to the drawer 332.

The return and tracking system 300 may require verification from a witness that a medical container was returned and/or the drawer 332 was emptied. For example, the return and tracking system 300 may prompt each of the healthcare professional and the witness to input information verifying that the medical container was placed in the drawer 332. For example only, the information may be manually entered (e.g., respective unique numeric identifiers assigned to the healthcare professional and the witness), scanned in using a barcode reader or card reader, retrieved biometrically (e.g., using a fingerprint scanner), etc.

The return and tracking system 300 may selectively prevent the drawer 332 from being opened or allow the drawer 332 to be opened. For example, the drawer 332 may include an actuator, locking mechanism, etc. that is remotely controllable by the return and tracking system 300. The return and tracking system 300 may open the drawer 332 in response to the healthcare professional requesting the drawer 332 to be opened to return a medication retainer or to empty the drawer 332.

The return and tracking system 300 may be in communication with one or more of the central inventory database 312, the medication base station 100, and/or the mobile workstation 200 to maintain and selectively update medication container return and tracking information. For example, the return and tracking system 300 may inform the central inventory database 312 to update the information after receiving confirmation from a healthcare professional that a medication was retrieved from the base station 100, that the medication was administered to the patient or otherwise disposed (i.e., "wasted"), that the corresponding medication container was returned to the base station 100, etc.

Although schematically shown separate from the medication base station 100 and the mobile workstation 200, the return and tracking system 300 may be a separate device or module (e.g., implemented within a handheld device), or may be implemented within the medication base station 100 and/or the mobile workstation 200 (e.g., within respective control modules 216).

Figure 4:
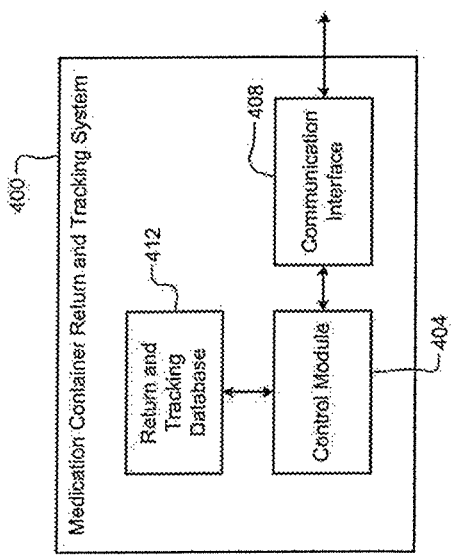
FIG. 4 is an example transport device according to the principles of the present disclosure.

FIG. 4 shows an example return and tracking system 400. The system 400 includes a control module 404, a communication interface 408, and a medication container return and tracking database 412. The communication interface 408 may implement a wired and/or wireless communication interface, user inputs, etc. for providing communication between the system 400 and other elements of the medication management system 304 and/or healthcare professionals.

The database 412 (implemented in, for example, nonvolatile memory) stores medication container return and tracking information as described above with respect to FIGS. 1-3. For example, the information may include, but is not limited to: information associating medication containers with respective identifiers, retrieved medications, healthcare professionals, patients, etc.; information indicating a return status of a medication container (e.g., retrieved from the base station 100 but not yet administered, retrieved from the base station 100 and administered but not yet returned, returned to the base station 100, etc.); information indicating a time that the medication was retrieved, a time that the medication was administered, a time that the medication container was retrieved, and/or an amount time since the medication was administered without the medication container being returned; and logs of all transactions for medications retrieved from the base station 100 and medication containers returned to the base station 100. In some implementations, the database 412 may be implemented within the medication inventory database 312.

The control module 404 implements various functions of the system 400 as described above in FIGS. 1-3, including, but not limited to, storing and retrieving the information in the database 412 and providing commands and information via the communication interface 408 based on the stored information. For example, the control module 404 controls interactions between the system 400 and the base station 100, the healthcare professional, and the medication inventory database 312.

Figure 5:
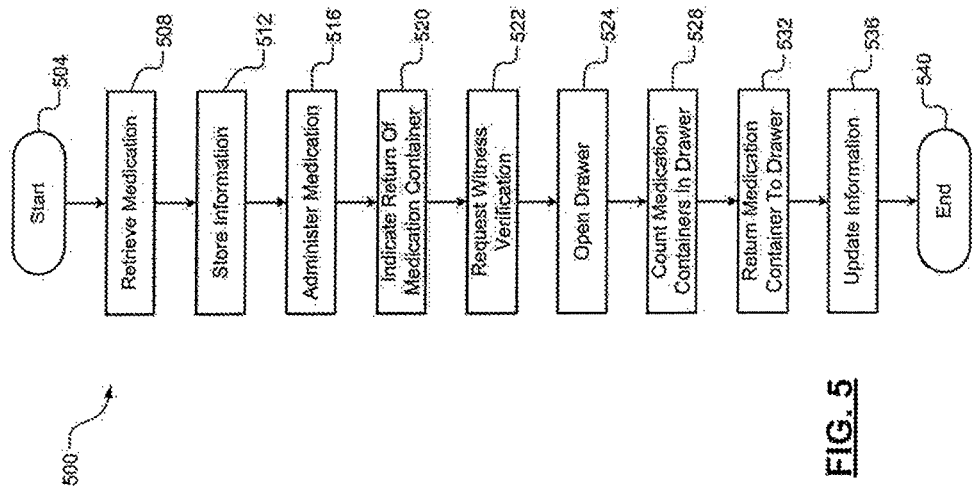
FIG. 5 is an example medication return and tracking method according to the principles of the present disclosure.

Referring now to FIG. 5, an example medication container return and tracking system 500 begins at 504. At 508, a healthcare professional retrieves a medication (e.g., from the base station 100). At 512, the method 500 stores information (e.g., in the database 412) indicating that the medication was retrieved. The information may include a time the medication was retrieved, information associating the medication with a particular healthcare professional and/or patient, information associating the container of the medication with a unique identifier, etc. At 516, the healthcare professional administers the medication.

At 520, the healthcare professional indicates intent to return the medication container. For example, at the base station 100, the healthcare professional scans the container, manually enters an identifier of the medication container, etc. At 522, the method 500 requests verification from a witness (e.g., an individual other than the healthcare professional returning the medication container). For example, the witness may be prompted to log in to the base station 100 and/or provide identification in another manner (e.g., scan a barcode, swipe a card in a card reader, provide biometric input, etc.). At 524, the method 500 opens and/or unlocks a drawer (e.g., a pre-assigned drawer, such as the drawer 332) assigned to returns of medication containers or assigns a drawer to be used for returns of medication containers. For example, the control module 404 provides a command to the base station 100 to open and/or unlock the drawer. In some embodiments, the method 500 verifies that the identifier does not correspond to a medication container that was already returned to the drawer prior to opening the drawer.

At 528, the healthcare professional provides an indication of a total number of medication containers within the drawer (e.g., a total number including the medication container that is being returned). The method 500 may verify that the provided number matches a stored number (e.g., a number stored by the database 412 to indicate the number of returned medical containers). If the provided number does not match the stored number, the method 500 may store a flag or other indicator to notify the central pharmacy of the discrepancy.

At 532, the healthcare professional returns the medical container to the drawer. For example, the healthcare professional returns the medical container, closes the drawer, and provides an indication that the medical container was returned (e.g., by manually responding to a prompt at the base station 100. In embodiments, the method 500 may also require a witness to verify that the medical container was returned and the drawer was closed. For example, the method 500 may prompt both the healthcare professional and the witness to input information verifying that the medication container was returned (e.g., by scanning respective barcodes on wristbands, cards, etc., requesting manual input of unique identifiers, etc.).

At 536, the method 500 updates the stored information to indicate that the medication container was returned. For example, the method 500 updates the database 412, the database 312, etc. The method 500 ends at 540.

In example embodiments, one or more of the above steps of the method 500 may be optional or omitted. For example, in some embodiments, requesting witness verification at 522 and/or requiring a count of the medication containers in the drawer at 528 may be selectively enabled and disabled.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A system, comprising:
   a database that stores information associated with a medication located in a base station, wherein the information includes an indication of whether the medication was returned to the base station subsequent to the medication being administered; and
   a control module remote from the base station that communicates with the base station and a mobile workstation, the control module configured to:
      determine a first return status when the medication is retrieved from the base station, the first return status indicating that the medication is transferred to the mobile workstation and has not yet been administered to a patient,
      store the first return status and identification information in the database, the identification information indicating an identity of the medication retrieved and an identity of a user that retrieved the medication,
      determine a second return status when a notification is received from the mobile workstation that the medication has been administered to the patient, the second return status indicating that the medication has been administered to the patient and has not yet been returned to the base station,
      store the second return status in the database,
      receive a request to return the retrieved medication,
      in response to the request, control the base station to unlock a drawer of the base station,
      determine whether the medication is returned to the drawer of the base station,
      confirm that the returned medication corresponds to the identity of the medication retrieved, and
      in response to the confirmation, determine a third return status indicating that the administered medication has been returned to the base station, and store the third return status in the database.

2. The system of claim 1, wherein the information further includes at least one of a time that the medication was retrieved from the base station, a time that the medication was administered to a patient, and a time that a container of the medication was returned to the base station.

3. The system of claim 1, wherein the information further includes an identifier associated with a container of the medication.

4. The system of claim 1, wherein the information further includes an identifier of the drawer in the base station.

5. The system of claim 4, wherein the drawer is assigned to be used for storing a container of the medication.

6. The system of claim 4, wherein the control module assigns the drawer to be used for storing a container of the medication in response to an indication that the container of the medication is being returned to the base station.

7. The system of claim 4, wherein the information includes a total number of a plurality of containers stored within the drawer.

8. The system of claim 4, wherein the control module provides a command to open the drawer in response to an indication that a container of the medication is being returned to the base station.

9. The system of claim 1, wherein the information includes respective indications from a healthcare professional and a witness that a container of the medication was returned to the base station.

10. A method comprising:
- storing, in a database, information associated with a medication located in a base station in communication with a mobile workstation, wherein the information includes an indication of whether the medication was returned to the base station subsequent to the medication being administered;
- determining, by a control module remote from the base station, a first return status when the medication is retrieved from the base station, the first return status indicating that the medication is transferred to the mobile workstation and has not yet been administered to a patient;
- storing, by the control module, the first return status and identification information in the database, the identification information indicating an identity of the medication retrieved and an identity of a user that retrieved the medication;
- determining, by the control module, a second return status when a notification is received from the mobile workstation that the medication has been administered to the patient, the second return status indicating that the medication has been administered to the patient and has not yet been returned to the base station;
- storing, by the control module, the second return status in the database;
- receiving, by the control module, a request to return the retrieved medication;
- in response to the request, controlling, by the control module, the base station to unlock a drawer of the base station;
- determining, by the control module, whether the medication is returned to the drawer of the base station;
- confirming, by the control module, that the returned medication corresponds to the identity of the medication retrieved; and
- in response to the confirmation, determining, by the control module, a third return status indicating that the administered medication has been returned to the base station, and storing the third return status in the database.

11. The method of claim 10, wherein the information further includes at least one of a time that the medication was retrieved from the base station, a time that the medication was administered to a patient, and a time that a container of the medication was returned to the base station.

12. The method of claim 10, wherein the information further includes an identifier associated with a container of the medication.

13. The method of claim 10, wherein the information further includes an identifier of the drawer in the base station.

14. The method of claim 13, further comprising assigning the drawer to be used for storing a container of the medication.

15. The method of claim 13, further comprising assigning the drawer to be used for storing a container of the medication in response to an indication that the container of the medication is being returned to the base station.

16. The method of claim 13, wherein the information includes a total number of a plurality of containers stored within the drawer.

17. The method of claim 13, further comprising providing a command to open the drawer in response to an indication that a container of the medication is being returned to the base station.

18. The method of claim 10, wherein the information includes respective indications from a healthcare professional and a witness that a container of the medication was returned to the base station.

* * * * *